United States Patent [19]
Mitra

[11] Patent Number: 4,822,599
[45] Date of Patent: Apr. 18, 1989

[54] ORAL COMPOSITIONS
[75] Inventor: Sekhar Mitra, Cincinnati, Ohio
[73] Assignee: The Procter & Gamble Company, Cincinnati, Ohio
[21] Appl. No.: 89,379
[22] Filed: Aug. 26, 1987
[51] Int. Cl.$^4$ .......................... A61K 7/18; A61K 7/16
[52] U.S. Cl. ........................................ 424/52; 424/49; 424/57
[58] Field of Search ....................... 424/49, 52, 57, 58
[56] References Cited
U.S. PATENT DOCUMENTS 3,927,201 12/1975 Baines et al. .......................... 424/54
3,927,202 12/1975 Harvey et al. ......................... 424/57
4,370,314 1/1983 Gaffar .................................... 424/54
4,590,066 5/1986 Parran, Jr. ............................. 424/52

FOREIGN PATENT DOCUMENTS 0040938 12/1981 European Pat. Off. .

Primary Examiner—Margaret Moskowitz
Assistant Examiner—F. T. Moezie
Attorney, Agent, or Firm—Richard C. Witte; Jack D. Schaeffer; Douglas C. Mohl

[57] ABSTRACT

Methods which reduce natural stain from teeth are described.

7 Claims, No Drawings

ORAL COMPOSITIONS

TECHNICAL FIELD

The present invention relates to methods using pyrophosphate compositions which reduce natural stain.

BACKGROUND OF THE INVENTION

Natural stain on teeth (human and lower animals) can be caused by a number of agents which are normally ingested such as coffee or tea. The stain forms on the pellicle film which forms on the teeth.

It has been surprisingly found by the present inventor that natural stain (contrasted with stain caused by antimicrobial agents) can be reduced by brushing with a paste containing a soluble pyrophosphate salt. While the prior art discloses compositions containing such salts, there is no suggestion that soluble pyrophosphates could reduce stain, natural or that caused by antimicrobials. As a matter of fact, U.S. Pat. No. 4,370,314, Jan. 25, 1983 to Gaffar indicates, in column 2 at lines 53-55, that soluble pyrophosphates would be ineffective against dental stain. This is supported by U.S. Pat. No. 3,927,201, Dec. 16, 1975 to Baines et al. wherein it is indicated that if sodium pyrophosphate decahydrate is used as an abrasive, the amount of the salt solubilized should be restricted to less than about 30% to enable the cleaning/abrasivity to be retained.

It is an object of the present invention to provide effective methods for reducing natural stain.

It is a further object of the present invention to provide methods which employ toothpastes containing soluble pyrophosphate salts as the stain reducing agent.

These and other objects will become more apparent from the detailed description which follows.

All percentages and ratios used herein are by weight unless otherwise specified.

SUMMARY OF THE INVENTION

It has been surprisingly found that natural stain can be removed from teeth by brushing with a toothpaste containing a soluble pyrophosphate source.

The compositions useful in the present invention comprise:

(a) from about 10% to about 70% by weight of a dental abrasive compatible with pyrophosphate ions and fluoride ions;

(b) an amount of a fluoride ion source sufficient to supply from about 50 ppm to about 3,500 ppm of fluoride ions;

(c) an amount of at least one soluble pyrophosphate source sufficient to provide at least about 1.0% $(P_2O_7)^{-4}$; and (d) from about 10% to about 95% water; wherein the pH of said composition is from about 6.0 to about 10.0.

The present method also provides the anticalculus benefits given by soluble pyrophosphate salts.

DETAILED DESCRIPTION OF THE INVENTION

The essential as well as optional components of the compositions of the present invention are described in the following paragraphs.

Dental Abrasive

The abrasives useful in the oral composition of the present invention include many different materials. The material selected must be one which has good compatibility with both fluoride ions and pyrophosphate ions. Suitable abrasives include $\beta$-phase calcium pyrophosphate prepared in accordance with the teaching of Schweizer, U.S. Pat. No. 3,112,247, Nov. 26, 1963. The $\beta$-phase calcium pyrophosphate is prepared by heating $\gamma$-phase calcium pyrophosphate to 700°–900° C. to change at least 50% of the $\gamma$-phase to $\beta$-phase and then immediately cooling. Another class of abrasives for use herein is the particulate thermosetting polymerized resins as described by Cooley et al in U.S. Pat. No. 3,070,510, Dec. 25, 1962. Suitable resins include, for example, melamines, phenolics, ureas, melamine-ureas, melamine-formaldehydes, urea-formaldehydes, melamine-urea-formaldehydes, cross-linked epoxies, and cross-linked polyesters.

Silica dental abrasives are also useful in the present compositions. The silica abrasive polishing material generally has an average particle size ranging between about 0.1 to 30 microns, preferably between 5 and 15 microns. The abrasive can be precipitated silica or silica gels such as the silica xerogels described in Pader et al, U.S. Pat. No. 3,538,230, Mar. 2, 1970 and DiGiulio, U.S. Pat. No. 3,862,307, Jan. 21, 1975, incorporated herein by reference. Preferred are the silica xerogels marketed under the tradename "Syloid" by the W. R. Grace & Company, Davison Chemical Division. Preferred precipitated silica materials are those marketed by the J. M. Huber Corporation under the tradename "Zeodent", particularly the silica carrying the designation Zeodent 119. These silica abrasives are described in Wason, U.S. Pat. No. 4,340,583, July 29, 1982, incorporated herein by reference.

Other suitable abrasives include alumina, and the insoluble metaphosphates such as insoluble sodium metaphosphate (IMP). Mixtures of abrasives can also be used. In any case, the total amount of abrasive in the toothpaste embodiments of this invention can range from 10% to 70% by weight of the toothpaste. Preferably, toothpastes contain from 10% to 50% by weight of abrasive.

The preferred abrasives are the $\beta$-phase calcium pyrophosphate of U.S. Pat. No. 3,112,247; alumina; insoluble metaphosphate; the resinous abrasives of U.S. Pat. No. 3,070,510; and the silica abrasives since they are more compatible with the agents. Most preferred are the silica abrasives.

Fluoride Ion Source

The second essential component of the oral compositions herein is a fluoride ion source. The number of such sources is great and includes those disclosed in U.S. Pat. No. 3,535,421, Oct. 20, 1970 to Briner et al., incorporated herein by reference. Typical materials include:

Stannous fluoride, potassium fluoride, lithium fluoride, cesium fluoride, ammonium fluoride, sodium fluoride, cupric fluoride, indium fluoride, stannous fluorozirconate, lead fluoride, ferric fluoride, nickel fluoride, paladium fluoride, silver fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride. $\Delta$-8,9-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N;-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N($\beta$-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2(N:N'-dimethylaminocarbonyl)-ethyl]-N-dodecyldiethylammonium fluoride, N-carboxymethyl-N-cicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, sodium monofluoro phosphate and mixtures thereof. Sodium fluoride is the preferred fluoride source.

The amount of the fluoride ion source should be sufficient to provide from about 50 ppm to 3500 ppm, preferably from about 100 ppm to 3000 ppm of fluoride ions.

Pyrophosphate Salts

The pyrophosphate salt used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. The amount of pyrophosphate salt useful in the present composition is any effective amount and is preferably enough to provide at least 1.0% $P_2O_7^{-4}$, preferably from about 2% to about 6%, to the compositions. It is to be appreciated that the level of $P_2O_7^{-4}$ is that capable of being provided to the composition (i.e., the theoretical amount at an appropriate pH) and that other pyrophosphate forms (e.g., $HP_2O_7^{-3}$) may be present when the salt is totally dissolved and a pH established.

The pyrophosphate salts are described in more detail in Kirk and Othmer, Encyclopedia of Chemical Technology, Second Edition, Volume 15, Interscience Publishers (1968), incorporated herein by reference.

Preferred pyrophosphate salts for use herein are tetrasodium pyrophosphate, tetrapotassium pyrophosphate, mixtures of tetrapotassium and tetrasodium pyrophosphates, mixtures of diakalimetal pyrophosphate salts with one or both of the tetra salts and diakalimetal salts alone. The latter two systems are preferred.

Water

Water is another essential component of the oral compositions of this invention. Water employed in the preparation of commercially suitable oral compositions should preferably be of low ion content and free of organic impurities. Water generally comprises from about 10% to about 95%, preferably from about 20% to about 95% of the toothpaste compositions of this invention.

Additional Components

In addition to the above described essential components, the compositions of this invention can contain a variety of optional, conventional oral composition components. Such optional ingredients include sudsing agents, binders, flavoring agents, humectants, sweetening agents, antiplaque agents, other anticalculus agents (the soluble pyrophosphate salts are such agents) coloring agents, pigments and other agents which do not form insoluble products with the fluoride or pyrophosphate ions.

A preferred optional ingredient is a sudsing agent. Suitable sudsing agents are those which are reasonably stable and form suds throughout a wide pH range, i.e., nonsoap anionic, nonionic, cationic, zwitterionic and amphoteric organic synthethic detergents. Sudsing agents of these types are described more fully in Agricola et al, U.S. Pat. No. 3,959,458, May 25, 1976, and in Haefele, U.S. Pat. No. 3,937,807, Feb. 10, 1976. Both of these patents are incorporated herein by reference.

Anionic sudsing agents useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, orthophosphonate.

The cationic sudsing agents useful in the compositions of the present invention can be broadly defined as quaternary ammonium compounds having one long alkyl chain containing from about 8 to about 18 carbon atoms such as lauryl trimethylammonium chloride; cetyl pyridinium chloride, cetyl trimethylammonium bromide; di-isobutylphenoxyethoxyethyl-dimethylbenzylammonium chloride; coconutalkyltrimethylammonium nitrate; cetyl pyridinium fluoride; etc.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains as anionic water-solubilizing group, e.g., carboxylate, sulfonate, sulfate, phosphate, or phosphonate.

The sudsing agent can be present in the compositions of this invention in an amount from about 0% to about 10% by weight of the total composition.

Flavoring agents can also be added to the instant compositions. Suitable flavoring agents include oil of wintergreen, oil of peppermint, oil of spearmint, oil of sassafras, and oil of clove. These agents are generally used at levels up to about 2%.

Binders can also be used with the toothpastes of the present inventions. Such binders include, for example, xanthan gum, carrageenan (Irish moss, Viscarin TP-5 which is a iota carrageenan), carboxy celluloses, and carboxyvinyl polymers. These binders are generally present at a level of from about 0.1% to 2%.

Bis-biguanide antiplaque agents can also optionally be added to the compositions of this invention. Such agents include chlorhexidine (1,6bis[$N^5$-p-chlorophenyl-$N^1$-biguanido]hexane), the soluble and insoluble salts thereof and related materials such as 1,2-bis($N^5$-p-trifluoromethylphenyl-$N^1$-biguanido)ethane and are described more fully in Haefele, U.S. Pat. No. 3,923,002, Jan. 20, 1976, Haefele, U.S. Pat. No. 3,937,807, Feb. 10, 1976, Procter & Gamble, Belgian Pat. No. 843,244, published Dec. 22, 1976, and Procter & Gamble, Belgian Pat. No. 844,764, published Jan. 31, 1977. These patents are incorporated herein by reference.

If present, the optional antiplaque agents generally comprise from about 0.1% to about 5% by weight of the compositions herein.

Other anticalculus agents which may be included in the present compositions include polyacrylic acid and other anionic linear polycarboxylate as well as other polymeric materials such as described in U.S. Pat. No. 3,429,963, Feb. 25, 1969 to Shedlovsky and U.S. Pat. No. 4,304,766, Dec. 8, 1981 to Chang, both incorporated herein by reference.

Another optional component of the compositions herein is a humectant. The humectant serves to keep the toothpaste compositions from hardening upon exposure to air and give a moist feel to the mouth. Certain humectants can also impart desirable sweetness of flavor to toothpaste compositions. The humectant, on a pure humectant basis, generally comprises from about 0% to 70%, preferably from about 0% to 55%, by weight of the compositions herein.

Suitable humectants for use in this invention include edible polyhydric alcohols such as glycerine, sorbitol, xylitol and propylene glycol. Sorbitol is frequently employed as a 70% aqueous solution known as Sorbo ®.

Sweetening agents can also be used in the compositions of this invention. Materials such as saccharin, dextrose, levulose, aspartame, D-tryptophan, dihydrochalcones, and acesulfame are suitable. Sodium cyclamate is another sweetening agent. Sweetening agents are generally used at levels of from about 0.1% to about 5% by weight.

The pH of the oral compositions herein is in the range of 6.0 to 10.0, preferably from 7.0 to 9.0. The pH is preferably achieved through a proper balancing of the pyrophosphate sources or by the addition of an alkaline or acidic agent.

The compositions of the present invention can be prepared by any method conventional in the art. The compositions of the present invention are used in conventional ways to brush teeth. Normally, brushing times range from about 10 seconds to about 60 seconds, preferably from about 30 seconds to about 45 seconds. The amount of paste used is usually from about 0.3 gms to about 1.2 gms.

The following examples are provided by way of illustration and not limitation.

EXAMPLE I

The following is an example of compositions useful in the present invention:

| Component | % |
|---|---|
| Sorbitol (70%) | 19.00 |
| Dye Solution | 0.300 |
| Precipitated Silica Abrasive | 22.0 |
| Sodium Fluoride | 0.243 |
| Flavor | 0.800 |
| Sodium Alkyl Sulfate (27.9% Aqueous Solution) | 4.0 |
| Sodium Acid Pyrophosphate | 2.68 |
| Tetrasodium Pyrophosphate | 1.834 |
| Tetrapotassium Pyrophosphate (65% Aqueous Solution) | 4.967 |
| Polyethylene Glycol | 4.000 |
| Xanthan Gum | 0.400 |
| Sodium Saccharin | 0.349 |
| Glycerin | 12.00 |
| Water | q.s. 100.000% |

EXAMPLE II

The following is another exemplary composition useful in the present invention:

| Component | % |
|---|---|
| Sorbitol (70%) | 32.0 |
| Sodium Saccharin | 0.28 |
| Color | 0.05 |
| Precipitated Silica Abrasive | 24.0 |
| Sodium Fluoride | 0.24 |
| Flavor | 1.04 |
| Sodium Alkyl Sulfate (27.9% Aqueous Solution) | 4.0 |
| Sodium Acid Pyrophosphate | 2.680 |
| Tetrasodium Pyrophosphate | 1.834 |
| Tetrapotassium Pyrophosphate (65% Aqueous Solution) | 4.967 |
| Carbomer 940[1] | 0.25 |
| Xanthan Gum | 0.800 |
| Titanium Dioxide | 0.525 |
| Polyethylene Glycol | 5.000 |
| Water | q.s. 100.000% |

[1] Carboxyvinyl polymer offered by B. F. Goodrich.

EXAMPLE III

The following is another example of a composition useful in the present invention:

| Component | % |
|---|---|
| Sorbitol (70%) | 35.00 |
| Sodium Saccharin | 0.280 |
| FD&C Blue #1 (1.0% Aqueous Solution) | 0.050 |
| Precipitated Silica Abrasive | 24.000 |
| Sodium Fluoride | 0.243 |
| Flavor | 1.044 |
| Sodium Alkyl Sulfate (27.9% Aqueous Solution) | 5.000 |
| Tetrasodium Pyrophosphate | 3.400 |
| Sodium Acid Pyrophosphate | 1.370 |

-continued

| Component | % |
|---|---|
| Carbomer 940 | 0.250 |
| Xanthan gum | 0.800 |
| Titanium Dioxide | 0.525 |
| Polyethylene Glycol 300 | 5.000 |
| Water | 23.038 |

EXAMPLE IV

The following is another example of a composition useful in the present invention:

| Component | % |
|---|---|
| Sorbitol (70%) | 27.645 |
| Sodium Saccharin | 0.260 |
| Sodium Fluoride | 0.243 |
| Flavor | 0.952 |
| Sodium Alkyl Sulfate (27.9% Aqueous Solution) | 4.000 |
| Tetrasodium Pyrophosphate | 3.580 |
| Sodium Acid Pyrophosphate | 1.220 |
| Xanthan Gum | 0.300 |
| Polyethylene Glycol 300 | 1.000 |
| Glycerin | 8.000 |
| Carrageenan | 0.800 |
| Calcium Pyrophosphate | 32.000 |
| Water | 20.000 |

All of the above compositions when used to brush the teeth will remove natural stain as well as reduce the incidence of calculus formation.

What is claimed is:

1. A method for reducing natural stain on teeth comprising brushing the teeth with a toothpaste comprising:
   (a) from about 10% to about 70% by weight of a dental abrasive compatible with pyrophosphate ions and fluoride ions;
   (b) an amount of a fluoride ion source sufficient to supply from about 50 ppm to about 3,500 ppm of fluoride ions;
   (c) an amount of at least one soluble pyrophosphate source sufficient to provide at least about 1.0% $(P_2O_7)^{-4}$; and
   (d) from about 10% to about 95% water; wherein the pH of said composition is from about 6.0 to about 10.0.

2. A method according to claim 1 wherein the soluble pyrophosphate salt is selected from the group consisting of tetraalkali metal pyrophosphate salts, dialkalimetal pyrophosphate salts and mixtures thereof.

3. A method according to claim 2 wherein the abrasive is selected from the group consisting of $\beta$-phase calcium pyrophosphate, alumina, insoluble metaphosphate, silica and mixtures thereof.

4. A method according to claim 3 wherein the fluoride ion source is sodium fluoride.

5. A method according to claim 4 wherein the pyrophosphate ion source is selected from the group consisting of tetrasodium pyrophosphate tetrapotassium pyrophosphate, disodium pyrophosphate and mixtures thereof.

6. A method according to claim 5 wherein the abrasive is a silica abrasive.

7. A method according to claim 1 wherein the composition also contains a humectant and a binder.

* * * * *